(12) United States Patent
Bhaumik et al.

(10) Patent No.: US 8,021,647 B2
(45) Date of Patent: Sep. 20, 2011

(54) IN VIVO OPTICAL IMAGING

(75) Inventors: Srabani Bhaumik, Niskayuna, NY (US); Eric Dustin Agdeppa, Fairview, NJ (US); June Klimash, Niskayuna, NY (US); Jeannette Christine DePuy, Watervliet, NY (US)

(73) Assignee: General Electric Company, Niskayuna, NY (US)

( * ) Notice: Subject to any disclaimer, the term of this patent is extended or adjusted under 35 U.S.C. 154(b) by 745 days.

(21) Appl. No.: 11/771,022

(22) Filed: Jun. 29, 2007

(65) Prior Publication Data

US 2009/0004116 A1    Jan. 1, 2009

(51) Int. Cl.
*A61B 10/00* (2006.01)
*A61B 5/00* (2006.01)

(52) U.S. Cl. ........ 424/9.6; 424/1.11; 424/1.65; 424/9.1; 424/9.2

(58) Field of Classification Search .................. 424/1.11, 424/1.65, 9.1, 9.3, 9.4, 9.5, 9.6, 9.7, 9.8
See application file for complete search history.

(56) References Cited

U.S. PATENT DOCUMENTS

| | | | |
|---|---|---|---|
| 6,217,847 B1 | 4/2001 | Contag et al. | |
| 6,534,041 B1 | 3/2003 | Licha et al. | |
| 7,662,973 B2 * | 2/2010 | Thomas et al. | 548/457 |
| 2003/0186348 A1 | 10/2003 | Thomas et al. | |
| 2004/0057903 A1 | 3/2004 | Hancu et al. | |
| 2006/0065146 A1 | 3/2006 | Mori | |

FOREIGN PATENT DOCUMENTS

| | | |
|---|---|---|
| WO | WO99/35288 | 7/1999 |
| WO | WO99/51270 | 10/1999 |
| WO | WO99/58161 | 11/1999 |

OTHER PUBLICATIONS

"Enzyme-Targeted Fluorescent Imaging Probes on a Multiple Antigenic Peptide Core", Galande et al., J. Med. Chem. 2006, 49, pp. 4715-4720.
"Near-Infrared Fluorescent Nanoparticles as Combined MR/Optical Imaging Probes", Lee Josephson et al., Bioconjugate Chem. 2002, 13, pp. 554-560.
"Near-Infrared Optical Imaging of Protease Activity for Tumor Detection", Umar Mahmood et al., Radiology 1999, pp. 213:866-870.
"In Vivo Imaging of Tumors with Protease-activated Near-Infrared Flurescent Probes", Ralph Weissleder et al., Nature Bootechnology, vol. 17, Apr. 1999, pp. 375-378.

* cited by examiner

*Primary Examiner* — D L Jones
(74) *Attorney, Agent, or Firm* — Jenifer E. Haeckl

(57) ABSTRACT

Provided herein are methods for imaging an optically labeled target cell implanted in vivo using a reporter construct that encodes an enzyme that is not endogenous to the target cell. The disclosed methods include the steps of: (a) introducing target cell transformed with non-endogenous enzyme into a mammalian subject; (b) contacting the transformed target cell with a cell-permeable soluble fluorescent dye; and (c) observing a fluorescent signal generated by the target cell present in the mammalian subject. In some embodiments, the non-endogenous enzyme comprises a nitroreductase. In some embodiments, the methods may also include the step of tracking the fluorescent target cells in the mammalian subject over time.

20 Claims, 4 Drawing Sheets

IN VIVO OPTICAL IMAGING

BACKGROUND

The use of fluorescence as a detection modality in biological assays is widespread and a diverse variety of procedures are available to generate fluorescence under assay conditions for detection by techniques such as fluorescence microscopy, fluorescence immunoassay and flow cytometry. Fluorescent signals may be generated using an enzyme to convert a non-fluorescent or substantially non-fluorescent substrate into a fluorescent product.

Such fluorescent enzyme substrates typically have two components that are coupled through a covalent linkage. One component is a fluorescent molecule that is capable of fluorescing by first accepting light energy and then emitting light energy. The other component is a masking group that prevents the fluorescent molecule from accepting or emitting light energy when the two components are covalently bound to one another, such that the molecule is non-fluorescent or substantially non-fluorescent. In the presence of an appropriate enzyme, cleavage of the covalent linkage takes place, thereby allowing the fluorescent molecule to absorb energy and emit fluorescence.

Tools exist for fluorescent imaging of cells in vivo using genetic reporters. Known reporters encode photoproteins that emit light that may be detected outside an animal's body by using optical cameras. With bioluminescence techniques, cells expressing a reporter gene product (e.g., luciferase) oxidize a substrate (e.g., D-luciferin), causing the substrate to emit light.

Optical imaging, which uses neither ionizing radiation nor radioactive materials, is emerging as a complement to nuclear imaging methods. The major limitation of light emitting probe is the high absorption and scattering that occur in biological tissues, which cause limited penetration of the light through the body. The currently available optical reporter genes emit light between about 400 nm and about 600 nm wavelengths.

SUMMARY OF THE INVENTION

Provided herein are method of imaging target cells implanted in vivo comprising: introducing target cell transformed with non-endogenous enzyme (e.g., NTR) into a mammalian subject (e.g., mouse, rat, rabbit, or human); contacting the transformed target cell with a cell-permeable soluble fluorescent dye; and observing a fluorescent signal generated by the target cell present in the mammalian subject.

In some embodiments, the cell-permeable soluble dye (e.g., a cyanine dye, such as Cy5, Cy5.5, Cy5S, CytoCy5S) may selected from a formula I or II

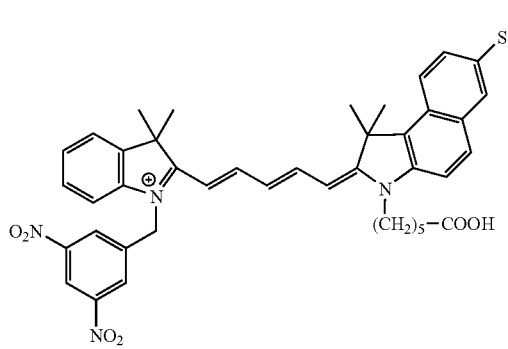

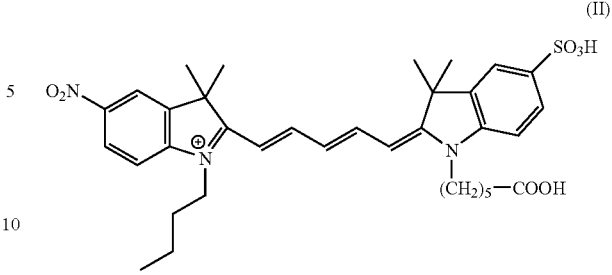

Transforming the target cell (e.g., a migratory cell or a stationary cell) with a nucleic acid encoding the non-endogenous enzyme. In some embodiments, target cell is a migratory cells selected from leucocytes, monocytes, dendritic cells, T-cells, or polymorphonuclear leukocytes (PMN's). The observing step may comprise quantitative, qualitative, or both quantitative and qualitative analysis of the signal generated by the target cell.

Also provided herein are methods of evaluating an effector agent comprising the steps of: introducing a target cell (migratory cell or a stationary cell) transformed with non-endogenous enzyme into a mammalian subject at a first location; contacting the transformed target cell with a cell-permeable soluble fluorescent dye (e.g., Cy5, Cy5.5, Cy5S, CytoCy5S, or combinations thereof); observing a fluorescent signal generated by the target cell present in the mammalian subject, administering a control cell into the mammalian subject at a second location in a body; contacting the transformed target cell with a cell-permeable soluble fluorescent dye; systemically introducing an effector agent (e.g., an anti-cancer therapeutic) into the mammalian subject; and observing the signals generated by at the first location and the second location.

In some embodiments, the non-endogenous enzyme comprises a nitroreductase. The cell-permeable soluble dye may be selected from a formula I or II

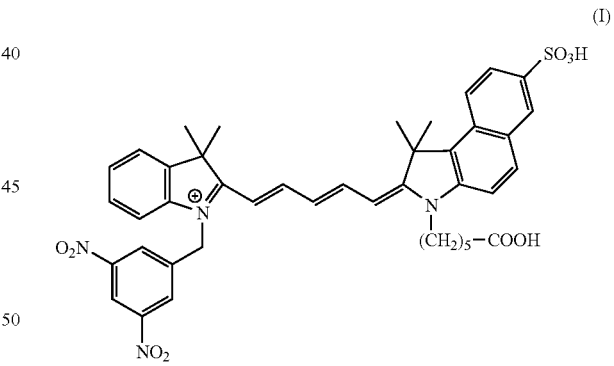

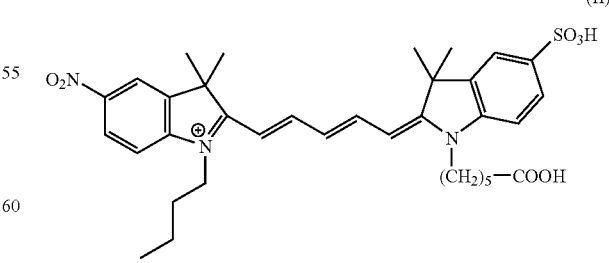

In some embodiments, the methods further comprising the step of transforming the target cell with a nucleic acid encoding the non-endogenous enzyme. The target cell is a migratory cell selected from leucocytes, monocytes, dendritic cells, T-cells, or PMN. In all embodiments, the observing step may comprise quantitative, qualitative, or both quantitative and qualitative analysis of the signal generated by the target cell.

DESCRIPTION OF THE FIGURES

These and other features, aspects, and advantages of the present invention will become better understood when the following detailed description is read with reference to the accompanying Figures wherein.

DETAILED DESCRIPTION

Figure 1:
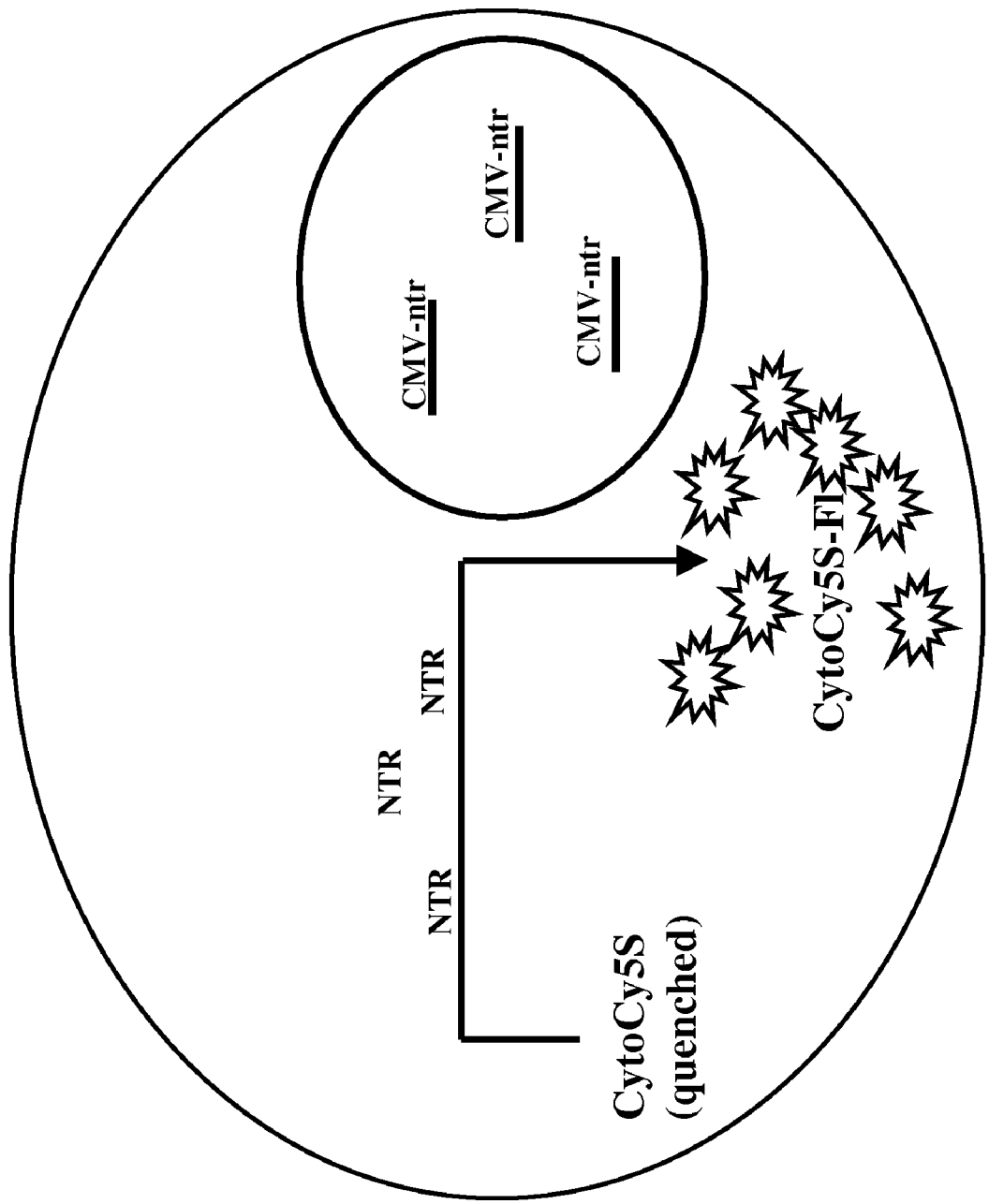
FIG. 1 depicts a representative scheme in which exogenous NTR proteins unquench a cell-permeable, quenched fluorescent dye.

The following detailed description is exemplary and not intended to limit the invention of the application and uses of the invention. Furthermore, there is no intention to be limited by any theory presented in the preceding background of the invention of the following detailed description of the drawings.

To more clearly and concisely describe and point out the subject matter of the claimed invention, the following definitions are provided for specific terms that are used in the following description and the claims appended hereto.

As used herein, the phrase "contacting the transduced target cell with a soluble dye" means any method of placing a transduced cell in contact with a soluble fluorescent dye such that the fluorescent dye is unquenched. Thus, the contacting step may comprise interaction of the target cell with the expression sequences and the fluorescent activatable substrate. In alternative embodiments, the contacting step may comprise introducing the fluorescent activatable dye into the body by for example, injection, aerosol, or ingestion.

As used herein, the phrase "ex vivo" with regard to the introduction of reporter constructs to a body refers to processes for obtaining and manipulating cells obtained from a subject outside the subject's body. In some embodiments, ex vivo processing includes removing cells (e.g., tumor cells or inflammatory response cells) from a subject's body, introducing reporter construct into the cells, and reintroducing the cells containing the reporter construct into the subject's body. In some embodiments, the cells that are removed from the subject may be enriched (e.g., by sorting, magnetic bead separation, or fractionation).

As used herein, the phrase "fluorescent dye" refers to dyes that are triggered by light to its active form. In some embodiments, the fluorescent dye is a cyanine dye for example, CytoCy5S, which is a quenched, cell permeant cyanine fluorescent analogue of Cy5Q that acts as a substrate for the NTR enzyme.

As used herein, the phrase "introducing a transduced target cell into an animal" refers to any method for introducing a transformed cell into an animal. Thus, transduced cells may be introduced into an animal by implantation or injection As used herein, the phrase "measuring signal generated by the target cell" refers any means for measuring a fluorescent signal, including for example using any optical reader device capable of measuring a signal generated by imaging an entire body (e.g., the GE Optix device) or an optical reader device attached to a surgical probe (e.g., a catheter equipped with an optical reader device).

As used herein, the phrase "operable expression sequences" refer to nucleic acid sequences encoding the gene products required for expression of a polypeptide demonstrating a desired functional activity. In some embodiments, the protein or protein fragment expresses reductase activity.

As used herein, the term "quenched" with reference to the soluble dyes refers to a chemical entity in which demonstrates fluorescent signal at or below background levels.

As used, herein the phrase "target cell" refers any cell that may be transduced with an enzyme capable of unquenching a quenched dye. Such cells include, for example, without limitation inflammatory response cells, epithelial cells, stem cells or cancer cells. In some embodiments, the target cell comprises a healthy cell. In alternative embodiments, the target cell comprises a diseased cell (e.g., tumor cell).

As used herein the term "transforming" generally refers to any method for transiently or stably introducing an exogenous nucleic acid into a cell. Thus, transformation may include methods such as electroporation, viral transfection, non-viral transfection, and naked DNA techniques.

As used, herein the term "unquenched" refers a chemical reaction that causes the activatable fluorescent dye to fluoresce. In one embodiment, the activatable fluorescent dye is unquenched by contacting the activatable fluorescent dye with a reductase enzyme, such as NTR.

Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

EMBODIMENTS

Provided herein are methods for imaging an optically labeled target cell implanted in vivo using a reporter construct that encodes an enzyme that is not endogenous to the target cell. The disclosed methods include the steps of: (a) introducing target cell transformed with non-endogenous enzyme into a mammalian subject; (b) contacting the transformed target cell with a cell-permeable soluble fluorescent dye; and (c) observing a fluorescent signal generated by the target cell present in the mammalian subject. In some embodiments, the non-endogenous enzyme comprises a nitroreductase (e.g., NTR). In some embodiments, the methods may also include the step of tracking the fluorescent target cells in the mammalian subject over time.

Nitroreductase Gene Expression

For use as a reporter gene, the nitroreductase gene may be isolated using art-recognized methods, for example by amplification from a cDNA library by use of the polymerase chain reaction (PCR). Once isolated, the nitroreductase gene may be inserted into a vector suitable for use with mammalian promoters in conjunction with and under the control of the gene regulatory sequence under study. Nitroreductase enzyme expression in the target cell may be achieved using an expression plasmid or other expression construct. Methods for preparing such expression constructs are well known to those skilled in the art. The vector containing the nitroreductase reporter and associated regulatory sequences may then be introduced into the host cell by transfection using art-recognized techniques using, for example, by electroporation, DEAE-Dextran treatment, or calcium phosphate treatment.

Fluorescent Dyes Useful in NTR Reporter Construct Systems

Examples of non-fluorescent or substantially non-fluorescent nitro group-containing cyanine dyes for use in the disclosed methods are described in U.S. Pat. No. 6,828,116 (Hamilton, A. L. et al) and have formulae (I) and (II).

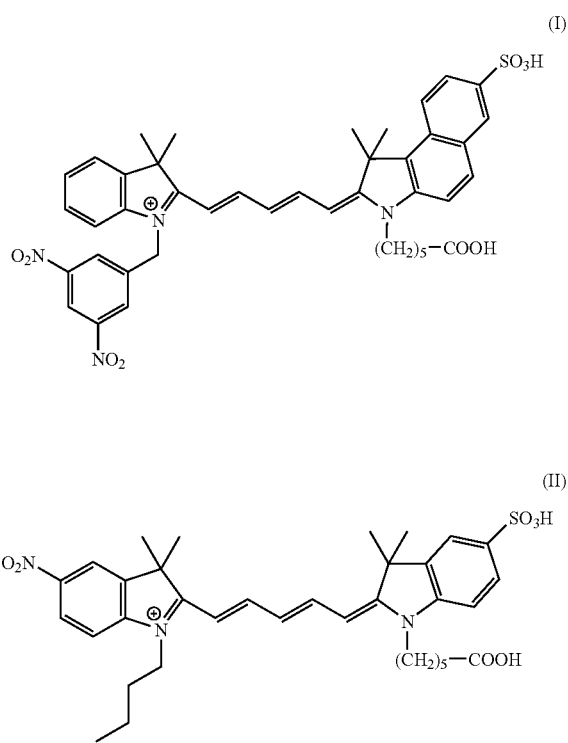

The fluorescent dye may include a masking group that is covalently attached to the dye, to modify one or more of the optical properties of the dye. For example, a fluorescent dye may be rendered non-fluorescent or substantially non-fluorescent. Following action by a nitroreductase, the nitro group of the masking moiety is reduced to a NHOH or NH2 group. This action results in cleavage of the dye from the masking group, thereby restoring the optical properties of the dye. The amount of change in the optical property upon such action may be correlated with the amount or activity of the nitroreductase.

In one aspect of the invention, there is provided a method for detecting nitroreductase gene expression, comprising the steps of:

(a) providing a host cell wherein the host cell has been transfected with a nucleic acid molecule comprising expression control sequences operably linked to a sequence encoding a nitroreductase;

(b) contacting the host cell with a substrate under conditions to promote nitroreductase activity and wherein the substrate comprises a compound of formula (I):

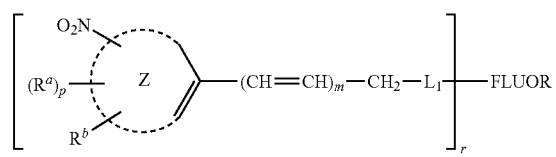

wherein groups Ra and Rb are attached to atoms of the Z ring system;

Z represents the a chain of linked atoms necessary to complete an aromatic or heteroaromatic ring system having five or six atoms selected from carbon atoms and optionally no more than two atoms selected from oxygen, nitrogen and sulphur; fluorescent is a fluorescent dye selected from xanthene, coumarin, and oxazine dyes; L1 is a bond or is an atom or a chain of 2 to 10 covalently linked atoms selected from the group consisting of carbon, nitrogen, oxygen and sulphur atoms; each Ra is hydrogen or may be selected from electron donating and withdrawing groups, and p is 0 or an integer from 1 to 3; Rb is hydrogen or is the group -L2-W, where L2 is a linker chain containing from 1-20 linked atoms and W is a fluorescent dye moiety or a quenching group; m is 0 or 1; and r is 1 or 2; and (c) detecting a change in an optical property upon cleavage of the fluorescent from the substrate;

wherein the change is a measure of the amount of nitroreductase gene expression.

The optical property that is detected is the intensity of emitted fluorescence, as a result of the action of the nitroreductase upon, and cleavage of the fluorescent dye moiety from the substrate. For example, the fluorescence emission intensity of the substrate may be determined in the absence of nitroreductase upon excitation of the fluorescent moiety and/or W at its typical excitation wavelength. Following combination of the substrate with nitroreductase enzyme, the fluorescence emission intensity is again measured at the emission wavelength of fluorescent and/or W and the change in measured fluorescence is determined. The change in fluorescence may be either an increase or a decrease in fluorescence intensity. Measurements of the amount of nitroreductase activity may be either quantitative (and thereby correlated to the amount of nitroreductase present), or the measure may be qualitative and be used to determine the presence or absence of nitroreductase.

Excitation of the nitroreductase substrate and measurement of fluorescence emission may also be performed over a range of wavelengths, so as to maximize emission signal and to distinguish between excitation and emission signals. Alternatively, the measured change in an optical property may be a change in fluorescence lifetime of the dye, before and after the action of the nitroreductase upon the composition. The change in fluorescence lifetime may also be used to distinguish the product of the enzyme reaction from the dye molecule used as the substrate. As a further alternative, the change in an optical property may be a change in the absorption maximum of the dye molecule, relative to the absorption maximum of the product. In some embodiments, the change in an optical property is an increase in the fluorescence intensity of the dye molecule, whereby the increase is a measure of the amount of nitroreductase activity.

In one embodiment, L1 is a single covalent bond linking the mono-nitro group-containing aralkyl or aralkenyl masking group and the fluorescent dye. Alternatively, L1 is an atom or a chain of 2 to 10 branched or unbranched covalently linked atoms linking the masking group and dye and is selected from the group consisting of carbon, nitrogen, oxygen and sulphur atoms. For example, L1 may comprise one or more atoms or groups selected from —CHR'—, —NR'—, —O—, —S—, —C(O)— and —C(S)—, where R' is hydrogen or C1-C4 alkyl.

Examples of suitable linking groups L1 include:
—O—C(O)—,
—O—C(O)—O—,
—O—C(O)—NH—, and
—O—C(O)—NH—CH2-.

Z in the compound of formula (I) is selected from phenyl, naphthyl, imidazolyl, oxazolyl and thiazolyl moieties. Preferably Z is a phenyl or an imidazolyl ring system. Preferably, the masking group attached to fluorescent is selected from:

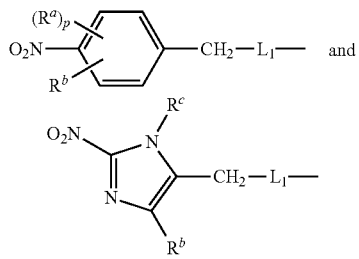

wherein Ra, Rb, Rc, L1 and p are hereinbefore defined, Rc is hydrogen or C1-C4 alkyl and m is 0.

Preferably, the substrate is a compound of formula:

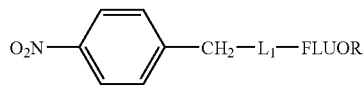

wherein L1 and FLUOR are as defined herein.

In one embodiment, FLUOR is selected from xanthene dyes including fluorescein derivatives, rhodamine derivatives and rhodol derivatives. In another embodiment, fluorescent is a coumarin dye. In a still further embodiment, FLUOR is an oxazine dye.

In some embodiments, one or more of groups Ra are selected from electron donating and withdrawing groups, for example, cyano, halogen, hydroxyl, C1-C4 alkyl, —NO2, —NHCO2Rd, —CO2H, —CO2Rd, —SH, C1-C4 alkylamino, and C1-C4 alkoxyl; where Rd is C1-C4 alkyl. Preferred groups Ra are either hydrogen or electron donating groups selected for their ability to enhance the rate of cleavage of the masking group from fluorescent, for example, C1-C4 alkyl, C1-C4 alkoxyl and C1-C4 alkylamino, preferably methyl, methoxyl, or methylamino. Halogen and halo groups may be selected from fluoro, chloro, bromo, and iodo.

The FLUOR may be selected from xanthene dyes (including their tautomeric forms), for example fluoresceins, rhodamines, rhodols and their derivatives; coumarin dyes; benzocoumarin dyes; and oxazine dyes. Suitable fluorescein dye derivatives will be well known to the skilled person and include but are not limited to fluorescein, 5-carboxyfluorescein, 6-carboxyfluorescein, 6-carboxy-4',5'-dichloro-2',7'-dimethoxyfluorescein, 5-(and-6)-carboxyfluorescein, 6-carboxy-2',4,4',5',7,7'-hexachlorofluorescein, 6-carboxy-2',4,7,7'-tetrachlorofluorescein, 2',7'-difluorofluorescein and eosin.

Suitable rhodamine dyes include but are not limited to: 5-carboxyrhodamine (Rhodamine 110-5), 6-carboxyrhodamine (Rhodamine 110-6), 5-carboxyrhodamine-6G (R6G-5 or REG-5), 6-carboxyrhodamine-6G (R6G-6 or REG-6), N,N,N',N'-tetramethyl-5-carboxyrhodamine, N,N,N',N'-tetramethyl-6-carboxyrhodamine (TAMRA or TMR), 5-carboxy-X-rhodamine and 6-carboxy-X-rhodamine (ROX). Xanthene dyes suitable for conjugation to the masking group are available commercially.

Suitable coumarin dyes include, but are not limited to, 7-hydroxy-coumarin, 7-hydroxycoumarin-4-acetic acid, 7-hydroxy-4-methylcoumarin, 7-amino-4-methylcoumarin and 7-amino-4-(trifluoromethyl)coumarin. Additional coumarin derivatives will be well known to the skilled person. Suitable oxazine dye derivatives include resorufin, Nile Blue, and cresyl violet.

Assaying Effector Agents

In some embodiments, the methods may be conducted in the presence of a effector agent whose effect on gene expression is to be determined. Typically, to assay the activity of a effector agent to modulate a cellular response, cells transfected with the nitroreductase reporter gene are incubated with the effector agent, followed by addition of a nitroreductase substrate of formula (I). The nitroreductase substrate is, or is rendered, permeable to cells under examination.

The effector agent may be, for example, any organic or inorganic compound such as a synthetic molecule or a natural product (e.g., a peptide or an oligonucleotide), or a may be an energy form (e.g., light or heat or other forms of electromagnetic radiation). The difference between the activity of the enzyme in the absence and in the presence of the agent is normalized, stored electronically and compared with a reference value. Thus, for example, the difference in activity may be stored as a percentage inhibition (or percentage stimulation) on an electronic database and this value compared with the corresponding value for a standard inhibitor of the enzyme in question. In this way, only effector agents meeting a certain pre-determined threshold (e.g., as being as effective or more effective than the reference compound) may be selected as being of interest for further testing.

The methods comprise the steps of: (a) performing an NTR activity assay in the presence and in the absence of the effector agent; and (b) determining the amount of nitroreductase gene expression in the presence and in the absence of the agent. Measurement of a difference in nitroreductase gene expression in the presence and in the absence of the agent is indicative of the effect of the effector agent on nitroreductase gene expression. Alternatively, the screening can be done by performing the method in the presence of a effector agent and comparing the value of the activity of the enzyme with a control value for the enzyme activity in the absence of the effector agent. The control value may be stored electronically in a database or other electronic format. After an appropriate period required for cleavage of the nitroreductase substrate and liberation of the fluorescent moiety, the fluorescence from the cells is measured at an emission wavelength appropriate for the chosen dye.

Measurements of fluorescence intensity may be made using instruments incorporating photo-multiplier tubes as detectors. Changes in fluorescence intensity may also be measured by means of a charge coupled device (CCD) imager (such as a scanning imager or an area imager) to image the animal. The measured fluorescence may be compared with fluorescence from control animal not exposed to the effector agent and the effects, if any, of the effector agent on gene expression modulated through the regulatory sequence is determined by the detection of the characteristic fluorescence in the test animal.

Examples of masked dye molecules that may be used in methods of the present invention are shown in Table 1.

TABLE 1

Examples of Masked Fluorescent Dyes

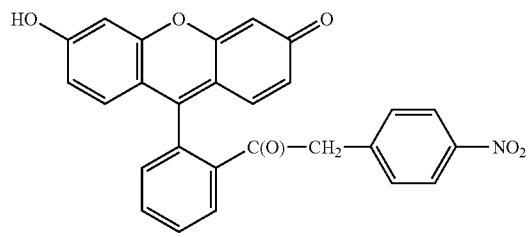
(II)

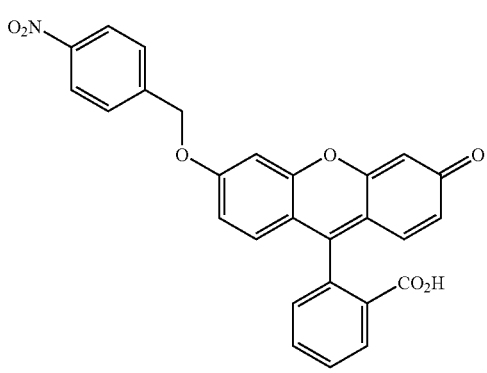
(III)

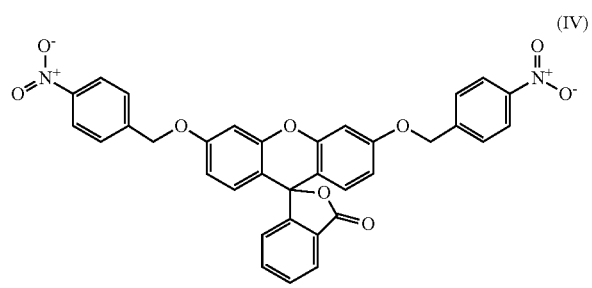
(IV)

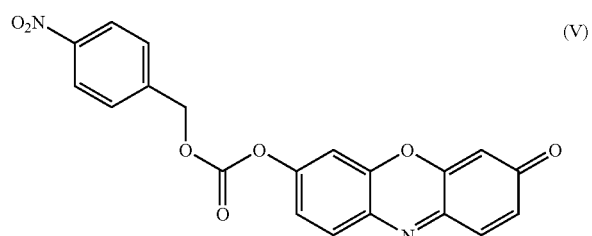
(V)

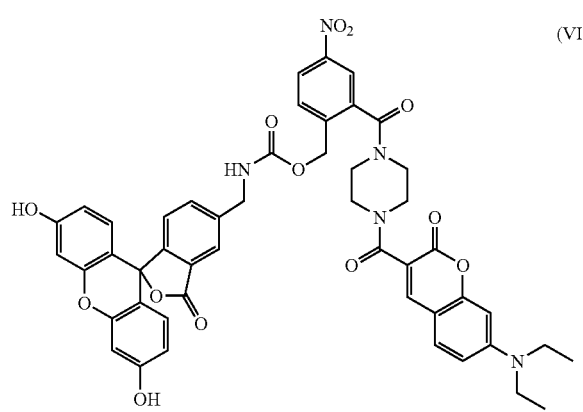
(VI)

In some embodiments, the nitroreductase substrate is, or is rendered, permeable to cells. In these embodiments, at least one of groups Rn comprises a cell membrane permeabilizing group, where n is 1, 2, 3, 4, 5, 6, 7, 8, 9, 10, 11, 12, 13, and 14. Membrane permeant compounds can be generated by masking hydrophilic groups of the dye moiety to provide more hydrophobic compounds. The masking groups can be designed to be cleaved from the substrate within the cell to generate the derived substrate intracellularly. Since the substrate is more hydrophilic than the membrane permeant derivative, it is trapped within the cell. Suitable cell membrane permeabilizing groups may be selected from acetoxymethyl ester that is readily cleaved by endogenous mammalian intracellular esterases.

The invention also provides a nitro group-containing compound for use as a reagent for preparing a nitroreductase enzyme substrate. Thus, in another aspect there is provided use of a reagent for preparing a masked reporter dye according to formula (I),

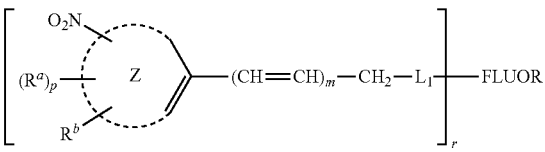
(I)

wherein groups Ra and Rb are attached to atoms of the Z ring system;

Z represents the a chain of linked atoms necessary to complete an aromatic or heteroaromatic ring system having five or six atoms selected from carbon atoms and optionally no more than two atoms selected from oxygen, nitrogen and sulphur; fluorescent is a fluorescent dye; L1 is a bond or is an atom or a chain of 2 to 10 covalently linked atoms selected from the group consisting of carbon, nitrogen, oxygen and sulphur atoms; each Ra is hydrogen or may be selected from electron donating and withdrawing groups, and p is 0 or an integer from 1 to 3; Rb is hydrogen or is the group -L2-W, where L2 is a linker chain containing from 1-20 linked atoms and W is a fluorescent dye moiety or a quenching group; m is 0 or 1 and r is 1 or 2. The reagent is a compound having the formula (II):

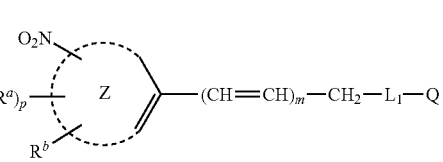
(II)

wherein groups Ra, Rb, Z, L1, p and m are hereinbefore defined and Q is a reactive group. In principle, any fluorescent dye may be derivatized by reaction of the dye with a compound according to formula (II). Suitable fluorescent dyes may be selected from xanthene dyes, coumarin dyes, oxazine dyes and cyanine dyes. Particularly preferred are xanthene (including fluorescein and derivatives, rhodamine and derivatives), coumarin and oxazine dyes.

One or more of groups Ra may be selected from electron donating and withdrawing groups, for example, cyano, halogen, hydroxyl, C1-C4 alkyl, —NO2, —NHCO2Rd, —CO2H, —CO2Rd, —SH, C1-C4 alkylamino, and C1-C4 alkoxyl; where Rd is C1-C4 alkyl. Preferred groups Ra are either hydrogen or electron donating groups selected for their ability to enhance the rate of cleavage of the masking group from fluorescent, for example, C1-C4 alkyl, C1-C4 alkoxyl and C1-C4 alkylamino, preferably methyl, methoxyl, or methylamino.

Q is a group chosen so as to be reactive with a complementary functional group of the fluorescent dye. Typically, Q is a leaving group selected from halogen, (for example chloro, bromo or iodo), C1-C4 alkoxy, for example methoxy and ethoxy, O-mesylate and O-triflate.

The NTR substrates are conveniently prepared by reacting a suitable nitro aryl compound with a selected dye in a suitable solvent medium and in the presence of a base. For example, 4-nitro benzyl bromide may be reacted with fluorescein in DMF in the presence of potassium carbonate, with displacement of bromide, to give the nitro aryl-dye conjugate. For the synthesis of the cassettes, a stepwise synthesis may be required, for example a suitable nitro aryl starting material such as 6-nitro phthalide may first be reacted with a dye (or a spacer moiety and then a dye), and subsequently conjugated to a second dye (where the first and second dyes may be the same or different).

In Vivo Imagining Using NTR Reporter Constructs with Fluorescent Dyes

The methods for optical imaging using NTR-Cy dye reporter constructs may be used for: (1) imaging tissue sections, (2) imaging tumor xenografts; or (3) tracking cells (e.g., stem cells or immune cells) in a live animal.

The disclosed methods may be used to track cells that have been transformed with the NTR gene ex vivo and subsequently introduced into a body. The transformed cells may be healthy cells (e.g., immune cells). Alternatively, the transduced and transduced cells may be diseased cells (e.g., tumor cells). The transduced cells may belong to the animal to be imaged or may belong to another animal.

When the transduced cells are exogenous, they may be derived from a histocompatible animal or a non-histocompatible animal depending on the particular application. Thus, for example, when the ability of a body to accept or reject an exogenous cells due to lack of histocompatibility for a specific protein, the MHC protein under study may be different from endogenous cells while the other MHC proteins are the same as endogenous cells.

Furthermore, the transduced cells may be migratory cells (inflammatory cells placed into a body, for example, intravascularly) or cells that substantially remain at the location where they are placed (e.g., tumor cells placed into a body). The mode of transduced cell introduction may be selected according to the preferred mobility of the cell. Thus, cells that are to be studied at the site of introduction may preferably be introduced by subdermal injection, placed in a surgical incised skin flap, or otherwise placed in tissue that does not include extensive vasculature or lymphatic structures. Similarly, cells that are to be studied in areas remote to the site of introduction, may preferably to introduced intravenously.

EXAMPLES

Practice of the invention will be still more fully understood from the following examples, which are presented herein for illustration only and should not be construed as limiting the invention in any way.

Example 1

Transformation of the Target Cells with the NTR Gene

Human colorectal carcinoma cell (LS174T cells), $2\times10^6$ were plated in 60 mm Petri plate and allowed to attain 70% confluency. The cells were transfected with CMV-ntr using Superfect reagent (Qiagen, Valencia, Calif.) following the protocol of stable transfection recommended by the manufacturer. The transfected cells were selected and maintained under selective media. The stable cell line was named as LS174T-NTR. In vitro live cell assay, using CytoCy5S revealed that the cells were stably transfected by NTR reporter gene. LS174T transfected with NTR genes shows fluorescent signal from cells when incubated with CytoCy5S.

Example 2

Substrate Selection

CytoCy5S dye (GE Healthcare) in powder form (1 mg) was dissolved in DMSO (100 µl) and further diluted in cell culture media 1:100 before adding to 2 cell lines SKOV control (SKOV-NTR⁻) and SKOV-NTR stably transformed (SKOV-NTR⁺) cells and LS174T control (LS174T-NTR⁻) and LS174T-NTR stably transformed (LS174T-NTR⁺). Both cell types were cultured in 96-well plate with 0.5 ng/well of CytoCy5S dye. Fluorescent signal emitted from the cells was confirmed using a Nikon TE2000-U fluorescent microscope and Incell 1000.

Example 3

Dye Entrapment

Figure 2:
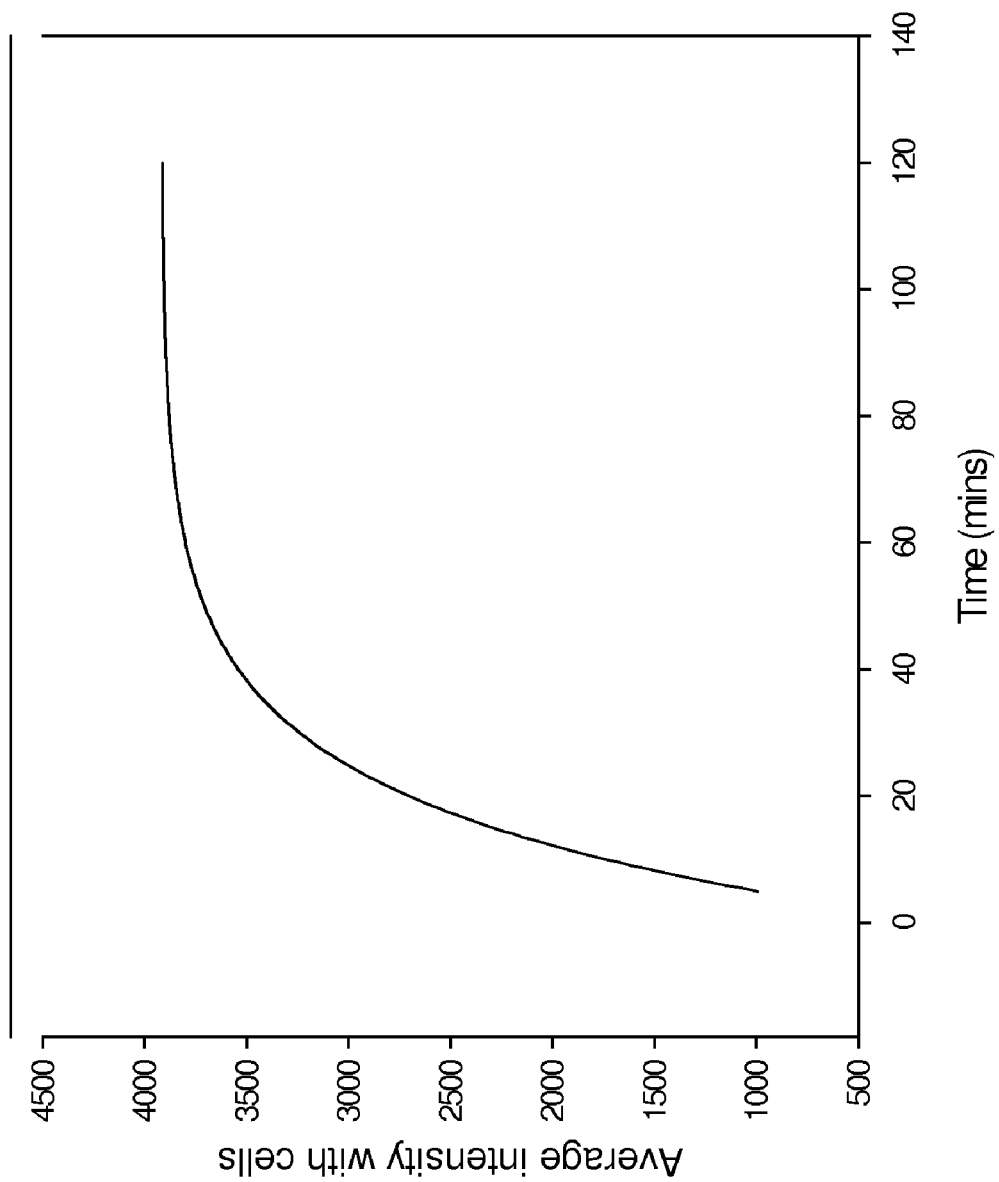
FIG. 2 shows kinetics of dye entrapment as described in Example 3 for LS174T cells.
Figure 3:
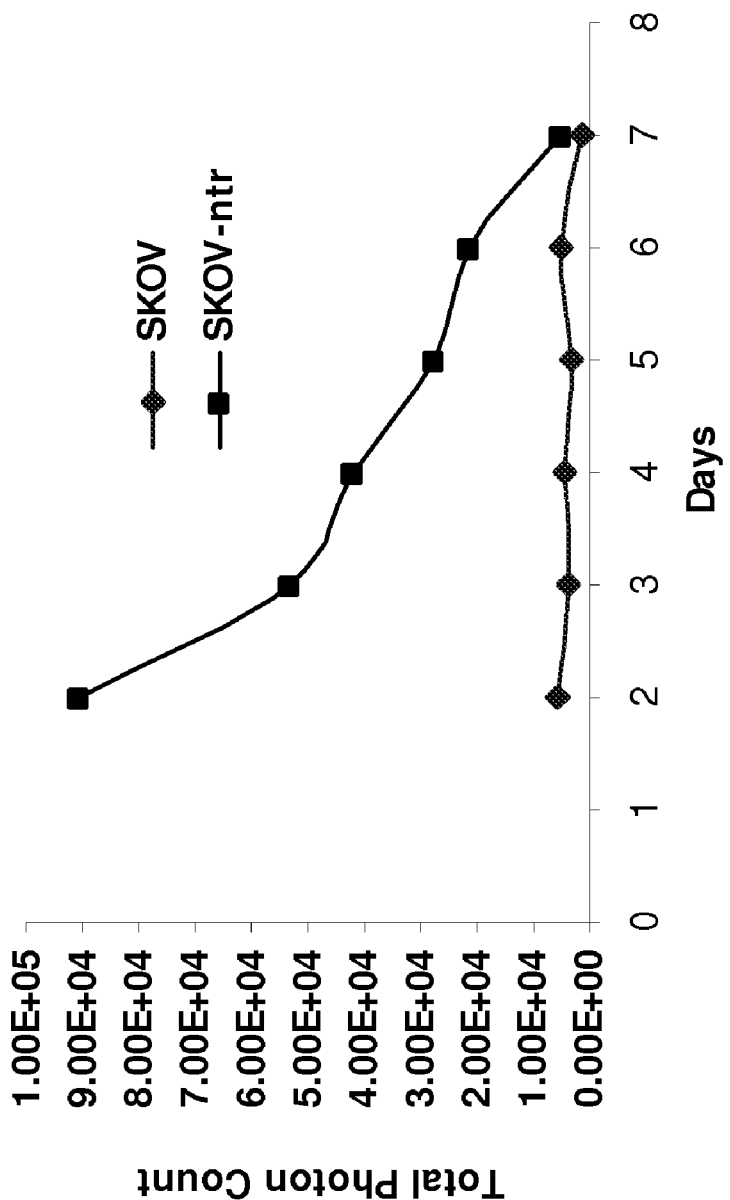
FIG. 3 a graphic depiction of Total Photon Counts (TPC) versus time, demonstrating that imagable signal persists for up to 8 days.

The cells treated with CytoCy5S dye were imaged live under Incell 1000 microscope using Cy5 filter for 120 minutes to follow the signal kinetics and signal was further quantified using a SPECTRAmax Specroflurimeter [Ex 620 nm, Em 670 nm]. The SKOV-NTR+ and LS174T-NTR+ cells demonstrated fluorescent signal and dye entrapment within the cell when viewed under Incell 1000. The fluorescent signal leveled off at around 50 minutes and remained constant for 120 minutes as shown in FIG. 2.

Similarly, the SKOV-NTR+ cells demonstrated significant signal of 1.9E+04 RLU when measured using the SPECTRAmax plate reader as compared to the SKOV-NTR− cells with 1.09+03 RLU.

Example 4

Machine Settings eXplore Optix

The eXplore Optix is an optical small animal scanner that has been designed to characterize, quantify and visualize cellular and molecular events in living animals using specific or non-specific fluorescent probes. This pre-clinical optical imager was based on time domain (TD) optical imaging technology. The equipment was fitted with built-in laser sources. The illumination occurs via a single fixed wavelength in the range of 440 nm to 785 nm. The choice of wavelengths ranged from the near-infrared wavelength region to the visible region. The system used was fitted with 440 nm, 635 nm, 657 nm, and 785 nm pulsed laser diodes coupled with emission filters.

The eXplore Optix has a staging area where the animal was placed on a bed and connected to anesthetic equipment. The door to the staging area was closed and locked before scanning. During imaging, the bed moved into a dark chamber (imaging chamber) that contained the laser sources, filters, and detectors. The image analysis was done using OptiView software. The signal collected was measured as Total Photon Count (TPC). Each animal was imaged using any 4 pulse laser diodes 440 nm, 630 nm, 650 nm, and 785 nm separately with vering LP (Laser Power), IT (integration time) and SS (scan step).

Example 5

Reducing Autofluorescence

Regular diet (2018S): Animals were fed with Tekland Global 18% Protein Rodent Diet (2018S) from Harlan Tekland. The 2018S chow was a fixed formula diet containing 18% protein and 5% fat that promotes gestation, lactation, and growth of rodents. It was a balanced diet supplemented with additional vitamins to ensure nutritional adequacy after autoclaving. Special feed was an alfalfa free chow from Harlan Tekland reported to down-regulate autofluorescence in mice. To minimize autofluorescence from the animal food, we fed the nude mice alfalfa-free chow for 2 weeks before imaging them. The control animal was fed with the regular chow and the animal in the right was fed with the special diet. Significant reduction (5.8 fold) of the food fluorescence observed the stomach region of nude mice fed with special diet was seen compared to animals fed with regular diet. Each animal was imaged with 670 nm pulsed laser diodes coupled with 700 nm emission filters with a LP (Laser Power) of 50 µW, IT (integration time) of 1.0s, and SS (scan step) of 3 mm.

Example 6

Optimizing Imagable Signal from Subcutaneous Sites

SKOV-NTR+ and SKOV-NTR− control cells were cultured in T25 flasks until they reached approximately 70% confluency. The flasks were then incubated with 0.5 µg/ml of CytoCy5S in 3 ml of media for 3 hours at 37° C. The cells were checked for the presence of fluorescent signals under Nikon microscope TE2000-U. The cells were trypsinized and the pellet washed twice with phosphate buffered saline (PBS). Two nude mice, under anesthesia, were injected with the pretreated cells: Animal 1 was injected with (a) $1 \times 10^6$ cells of SKOV-NTR+ on right shoulder and $1 \times 10^6$ SKOV-NTR− control cells on the left shoulder. Animal 2 had (b) $2.5 \times 10^6$ cells of SKOV-NTR+ on right shoulder and $2.5 \times 10^6$ SKOV-NTR− control cells on the left shoulder. Animals were imaged under eXplore Optix (small animal optical equipment) for 5 minutes immediately after implanting tumor cells. Nude mice implanted with both $1 \times 10^6$ cells and $2.5 \times 10^6$ cells showed signal that was imagable from the subcutaneous location. The signal captured from $2.5 \times 10^6$ SKOV-NTR+ cells were 3.7 fold higher that those reported from $1 \times 10^6$ SKOV-NTR+ cells.

Example 7

In Vivo Tracking of Pretreated Cell

SKOV-NTR+ and SKOV-NTR− control cells were pretreated with fluorescent dye (CytoCy5S) in vitro as described above. The cells were trypsinized, washed, counted, and checked for signal under fluorescent microscope. $1 \times 10^6$ SKOV-NTR+ cells were implanted on the left and $1 \times 10^6$ SKOV-NTR− control cells on the right shoulder region of the nude mouse. The animal was imaged for next 8 days to determine the longevity of the signal that could be tracked from pretreated cells from the subcutaneous tumor location.

The pretreated SKOV-NTR+ cells implanted at subcutaneous site showed imagable signals up to 8 days. The signal diminishes with time. SKOV-NTR+ did not develop into tumors whereas SKOV-NTR− control cells developed fast and aggressive tumors. The down-regulation of signal from the tumor site may be due to cell death at the cell at SKOV-NTR+ at the tumor site. These results show that the signal entrapping in the cells may be used to track cells over time.

Example 8

In Vivo Tumor Xenograft Imaging with SKOV Cells

Figure 4:
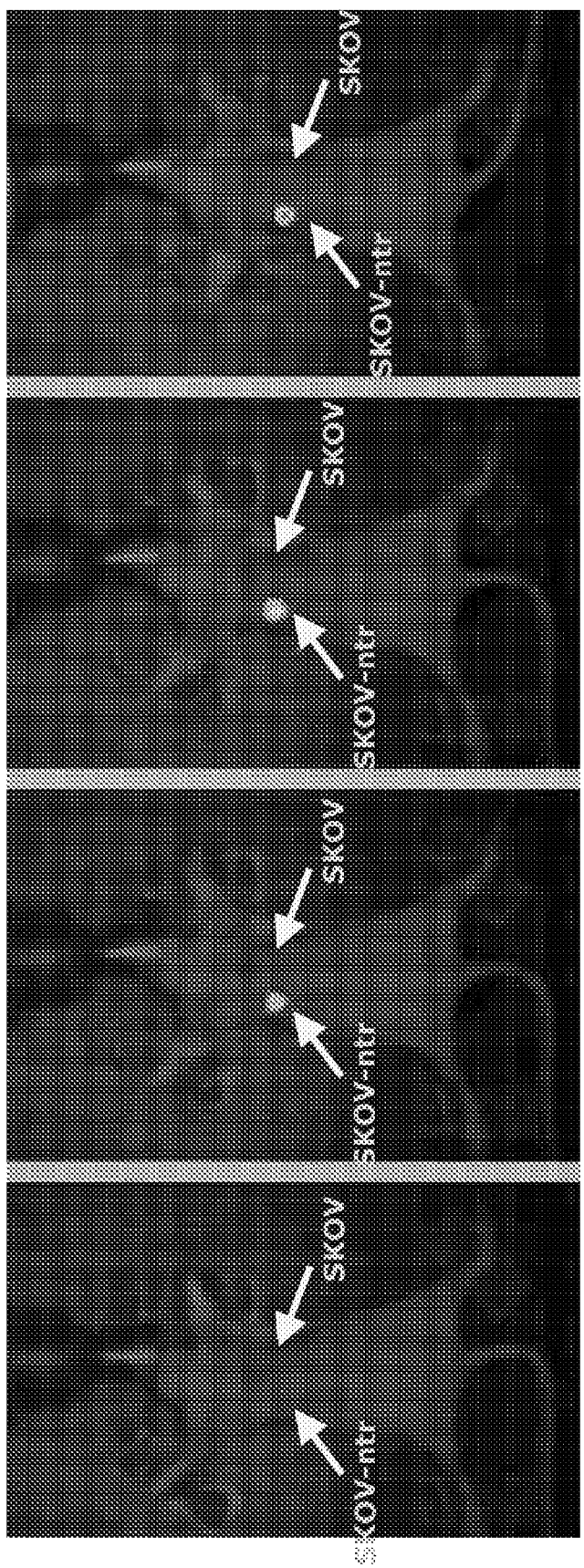
FIG. 4 shows optical images a single animal at intervals of: 10 minutes (panel 4A); 30 minutes (panel 4B); 100 minutes (panel 4C); and 120 minutes (panel 4D).

SKOV-NTR+ and SKOV-NTR− control cells were implanted on the left and right shoulder of a nude mouse at $5 \times 10^6$ cells and $0.5 \times 10^6$ concentrations, respectively. Tumors were allowed to grow for 8 days. 100 µl of CytoCy5S (2 mg/ml stock) was injected intraperitoneally. Nude mice were anesthetized with 2% isoflurane and scanned under eXplore Optix to detect signal from the tumor site as shown in FIG. 4.

Example 9

Kinetics Studies

SKOV-NTR$^+$ and SKOV-NTR$^-$ control cells were implanted in nude mice at $5 \times 10^6$ cells and $0.5 \times 10^6$ concentrations as mentioned above. Tumors were allowed to develop for 8 days. 100 µl of CytoCy5S (2 mg/ml) was injected intraperitoneally. Nude mice were anesthetized with isoflurane and scanned under Optix. The mouse was imaged every 10 minutes, from 10 minutes to 120 minutes to measure the signal kinetics (FIG. 4). Signal upregulation from the tumor bearing SKOV-NTR$^+$ cells relative to the SKOV-NTR$^-$ control cells was recorded. No signal appeared from the SKOV control tumor. The kinetics shows steady signal upregulation from 10 minutes, peaking around 40 minutes. This study correlates with the signal kinetics done in cell culture. Thus, peak signal may be viewed about 1 hour after substrate injection, during which the quenched dye is converted to its fluorescent form.

Equivalents

The invention may be embodied in other specific forms without departing from the spirit or essential characteristics thereof. The foregoing embodiments are therefore to be considered in all respects as illustrative rather than limiting on the invention described herein. The scope of the invention is thus indicated by the appended claims rather than by the foregoing description, and all changes that come within the meaning and range of equivalency of the claims are therefore intended to be embraced therein.

We claim:

1. A method of imaging target cells implanted in vivo comprising:
   (a) introducing target cells transformed with a non-endogenous enzyme into a mammalian subject, wherein the non-endogenous enzyme comprises nitroreductase;
   (b) contacting the transformed target cells with a cell-permeable soluble quenched fluorescent dye comprising a cyanine dye; and
   (c) observing a fluorescent signal generated by the target cells present in the mammalian subject.

2. The method of claim 1, wherein the cell-permeable soluble dye is selected from formula I or II:

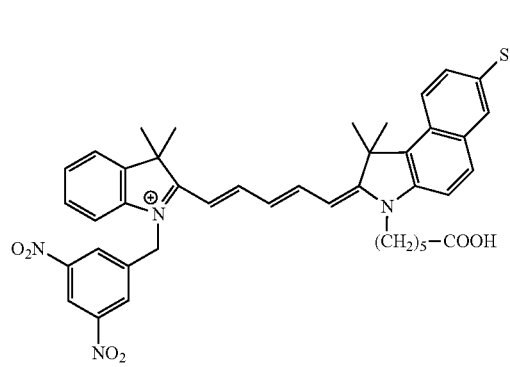
(I)

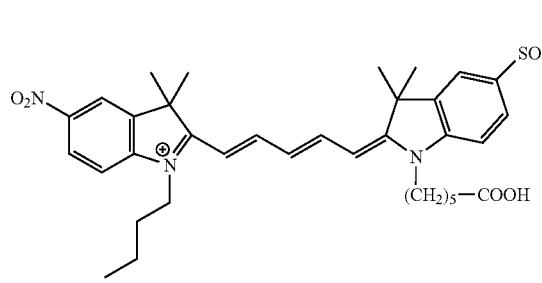
(II)

3. The method of claim 1, wherein the quenched soluble dye is selected from the group consisting of Cy5S, CytoCy5S and combinations thereof.

4. The method of claim 1, further comprising the step of transforming the target cell with a nucleic acid encoding the non-endogenous enzyme.

5. The method of claim 1, wherein the target cell is a migratory cell or a stationary cell.

6. The method of claim 5, wherein the target cell is a migratory cell selected from monocytes, dendritic cells, T-cells, or polymorphonuclear leukocytes (PMN's).

7. The method of claim 1, wherein the mammalian subject is selected from mouse, rat, rabbit, or human.

8. The method of claim 1, wherein the observing step comprises quantitative, qualitative, or both quantitative and qualitative analysis of the signal generated by the target cells.

9. A method of evaluating an effector agent comprising the steps of:
   (a) introducing target cells transformed with a non-endogenous enzyme into a mammalian subject, wherein the non-endogenous enzyme comprises a nitroreductase;
   (b) contacting the transformed target cell with a cell-permeable soluble quenched fluorescent dye comprising a cyanine dye;
   (c) observing the fluorescent signal generated by the target cells present in the mammalian subject,
   (d) introducing target cells transformed with the non-endogenous enzyme into a mammalian subject;
   (e) contacting the transformed target cell with the cell-permeable soluble fluorescent dye;
   (f) systemically introducing an effector agent into the mammalian subject; and
   (g) comparing the signal generated by the target cells present in the mammalian subject subjected to the effector agent to that observed in step (c).

10. The method of claim 9, wherein the cell-permeable soluble dye is selected from formula I or II:

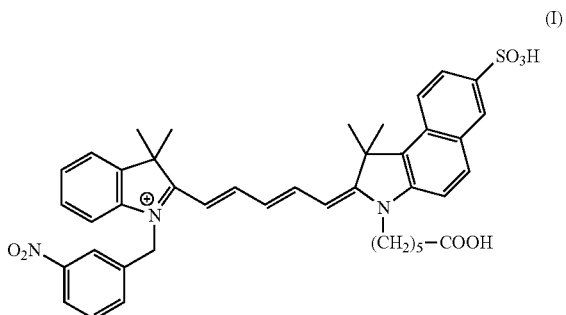
(I)

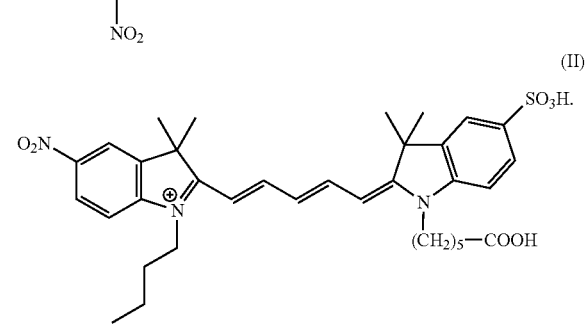
(II)

11. The method of claim 9, wherein the quenched soluble dye is selected from the group consisting of Cy5S, CytoCy5S and combinations thereof.

12. The method of claim 9, further comprising the step of transforming the target cells with a nucleic acid encoding the non-endogenous enzyme.

13. The method of claim 9, wherein the target cell is a migratory cell or a stationary cell.

14. The method of claim 13, wherein the target cell is a migratory cell selected from monocytes, dendritic cells, T-cells, or PMN's.

15. The method of claim 9, wherein the mammalian subject is selected from mouse, rat, rabbit, or human.

16. The method of claim 9, wherein the observing step comprises quantitative, qualitative, or both quantitative and qualitative analysis of the signal generated by the target cells.

17. The method of claim 9, wherein the effector agent comprises an anti-cancer therapeutic.

18. The method of claim 5, wherein the target cell is a leukocyte.

19. The method of claim 13, wherein the target cell is a leukocyte.

20. The method of claim 1, further comprising the steps of:
   (d) introducing target cells transformed with the non-endogenous enzyme into a mammalian subject;
   (e) contacting the transformed target cell with the cell-permeable soluble fluorescent dye;
   (f) systemically introducing an effector agent into the mammalian subject; and
   (g) comparing the signals generated by the target cell present in the mammalian subject subjected to the effector agent to that observed in step (c).

* * * * *